(12) United States Patent
Johnson et al.

(10) Patent No.: US 11,227,140 B2
(45) Date of Patent: Jan. 18, 2022

(54) SAMPLE CAPTURE UNIT

(71) Applicant: INTELLIGENT FINGERPRINTING LIMITED, Cambridge (GB)

(72) Inventors: Jonathan Johnson, Cambridge (GB); Mark John Henry Hudson, Cambridge (GB)

(73) Assignee: INTELLIGENT FINGERPRINTING LIMITED, Cambridge (GB)

( * ) Notice: Subject to any disclaimer, the term of this patent is extended or adjusted under 35 U.S.C. 154(b) by 264 days.

(21) Appl. No.: 16/499,118

(22) PCT Filed: Mar. 27, 2018

(86) PCT No.: PCT/GB2018/000051
§ 371 (c)(1),
(2) Date: Sep. 27, 2019

(87) PCT Pub. No.: WO2018/178614
PCT Pub. Date: Oct. 4, 2018

(65) Prior Publication Data
US 2021/0012085 A1   Jan. 14, 2021

(30) Foreign Application Priority Data
Mar. 30, 2017   (GB) ...................................... 1705125

(51) Int. Cl.
*G06K 9/00* (2006.01)
*A61B 5/1172* (2016.01)
(Continued)

(52) U.S. Cl.
CPC ........ *G06K 9/00087* (2013.01); *A61B 5/1172* (2013.01); *G01N 33/4875* (2013.01); *H01J 49/0409* (2013.01)

(58) Field of Classification Search
CPC ............ G06K 9/00087; G06K 9/00885; A61B 5/1172; A61B 10/0096; G01N 33/4875; H01J 49/0409; B01L 3/508
See application file for complete search history.

(56) References Cited

U.S. PATENT DOCUMENTS

| | | | |
|---|---|---|---|
| 2007/0087357 A1* | 4/2007 | Clark | G01N 33/54386 435/6.11 |
| 2016/0199044 A1* | 7/2016 | Hudson | A61B 5/1172 600/562 |

FOREIGN PATENT DOCUMENTS

| | | |
|---|---|---|
| GB | 2517737 A | 3/2015 |
| JP | 2016535264 A | 11/2016 |

(Continued)

*Primary Examiner* — Abhishek Sarma
(74) *Attorney, Agent, or Firm* — Lando & Anastasi, LLP (57) ABSTRACT

A sample capture unit comprising a housing defining an enclosed substrate chamber containing a substantially planar sample-capture substrate extending in a plane for receiving a skin-print thereon. The housing comprises: a first part having an aperture providing access to the substrate chamber for depositing a skin-print on the sample-capture substrate; and a second part movable relative to the first part, from a first position in which the aperture is uncovered so as to allow receipt of a sample on the sample-capture substrate, and into a second position in which the aperture is covered, thereby preventing access to the substrate chamber; the housing further comprises a retaining mechanism configured to retain the second part in the second position; and an element having a perimeter defined by a line of frangibility, which enables irreversible detachment of at least a part of the element so as to create an access port dimensioned to allow removal of the sample-capture substrate.

20 Claims, 7 Drawing Sheets

(51) Int. Cl.
*G01N 33/487* (2006.01)
*H01J 49/04* (2006.01)

(56) References Cited

FOREIGN PATENT DOCUMENTS

| | | |
|---|---|---|
| WO | 2013126824 A1 | 8/2013 |
| WO | 2016135497 A1 | 9/2016 |

* cited by examiner

SAMPLE CAPTURE UNIT

CROSS-REFERENCE TO RELATED APPLICATIONS

This application is a U.S. national phase application and claims the benefit of priority under 35 U.S.C. § 371 of International Patent Application Serial No. PCT/GB2018/000051, titled "A SAMPLE CAPTURE UNIT" and filed on Mar. 27, 2018, the contents of which are hereby incorporated herein by reference in their entireties for all purposes, and which in turn claims priority to United Kingdom Patent Application Serial No. 1705125.1, filed on Mar. 30, 2017.

BACKGROUND

An impression left by the friction ridges of human skin, such as the skin of a human finger contains information regarding the identity of the human. It is widely known that the appearance of the impression of the human finger, known as a fingerprint, is unique to each human and may be used to confirm the identity of the human. The appearance of the impression of the skin of other human body parts may also be unique to each human and so may also be used to confirm the identity of the human. Such impressions of human skin, when not specific to the skin of the human finger, may be called skin-prints.

In addition to the appearance of the impression left by human skin, the impression may contain chemical species which themselves may be detected in order to obtain further information.

For example, when a human intakes a substance (e.g. by ingestion, inhalation or injection) the substance may be metabolised by the human body giving rise to secondary substances known as metabolites. The presence of a particular metabolite can be indicative of a specific intake substance. The intake substance and/or metabolites may be present in sweat and, as such, may be left behind in a skin-print, e.g. a fingerprint. Detection of such metabolites in a skin-print can be used as a non-invasive method of testing for recent lifestyle activity such as (but not limited to) drug use, or compliance with a pharmaceutical or therapeutic treatment regime.

Importantly, the taking of a skin-print is much simpler than obtaining other body fluids such as blood, saliva and urine, and is more feasible in a wider range of situations. Not only this but since the appearance of the skin-print itself provides confirmation of the identity of the person providing the skin-print, there can be greater certainty that the substance or substances in the skin-print are associated with the individual. This is because substitution of a skin-print, particularly a fingerprint, is immediately identifiable from appearance whereas substitution of, for example, urine, is not immediately identifiable from appearance. As such, testing for one or more substances in a skin-print provides a direct link between the one or more substances and the identity of the human providing the skin-print.

The applicant has developed a lateral flow skin-print analysis technique as described in WO 2016/012812, published 28 Jan. 2016. The applicant has also developed a device (e.g. a cartridge) for performing lateral flow analysis of skin-prints. This is described in WO 2016/135497, published 1 Sep. 2016.

In some circumstances, it may be beneficial to provide a second test either as an alternative, or in addition, to a lateral flow test. For example, the second test may provide confirmation of the lateral flow test result via an alternative technique. This may be particularly advantageous where the lateral flow test provides a positive result. It may be that the second test may enable a more detailed quantitative result to be obtained. Such a test may be known as a confirmation test.

In addition to lateral flow techniques, the applicant has demonstrated various alternative techniques for analysing skin-prints, including the use of mass spectrometry. One or more such techniques may require a skin-print sample to be deposited on a planar substrate which can be provided for the analysis.

Whatever the analysis technique, confidence in the accuracy of a test is paramount. It is important, therefore, that steps are taken to prevent contamination (either innocently or maliciously) of a substrate on which a skin-print is collected, either before or after the impression of the skin is taken. The substrate must be accessible only for the short period during which the skin-print is taken. In addition to taking steps to prevent contamination, the provision of tamper-evident features that immediately indicate a likelihood of contamination is also important.

The applicant previously developed a sample capture unit as described in WO 2015/028785, published 5 Mar. 2015. This sample capture unit comprises features to prevent contamination and tamper-evident features that provide immediate evidence of tampering. This sample capture unit is specifically intended for optical analysis of an optically transparent substrate using a machine that opens the sample capture unit and analyses the sample it without removing the substrate from the unit.

STATEMENTS OF INVENTION

Against this background there is provided a sample capture unit comprising a housing defining an enclosed substrate chamber containing a substantially planar sample-capture substrate extending in a plane for receiving a skin-print, the housing comprising:
  a first part having an aperture providing access to the substrate chamber for depositing a skin-print on the sample-capture substrate;
  a second part movable relative to the first part:
    from a first position in which the aperture is uncovered so as to allow receipt of a sample on the sample-capture substrate; and
    into a second position in which the aperture is covered, thereby preventing access to the substrate chamber;
  a retaining mechanism configured to retain the second part in the second position;
  wherein the housing further comprises an element having a perimeter defined by a line of frangibility which enables irreversible detachment of at least a part of the element so as to create an access port dimensioned to allow removal of the sample-capture substrate.

In this way, it is possible to deposit a sample such as a fingerprint on the substrate and close the shutter providing confidence that the substrate is secure from damage and contamination. Subsequent access to the substrate is provided only by irreversible detachment of at least a part of the element (or by more comprehensive destruction of the sample capture unit) which is immediately self-evident. In this way, when a sample collected in the field arrives at a facility for testing the sample, the facility can be confident that the sample has been inaccessible since closure of the shutter.

The element may be a snap-off cover, and the snap-off cover may be partially or fully detachable from the housing by irreversible breaking at the line of frangibility.

The housing may comprise an exterior shell and the element comprises a tab that protrudes beyond the exterior shell by which a user may apply a force to the element to effect detachment of at least a part of the element by breaking at the line of frangibility.

The second part of the housing may comprise a shutter slidable with respect to the first part of the housing.

The substantially planar sample-capture substrate may have a length and a width in the plane, wherein the width is smaller than the length, and wherein the access port has a dimension that is larger than the width of the sample-capture substrate.

The aperture may be laterally offset from the element in the plane.

The enclosed substrate chamber may comprise one or more locator pins and the sample-capture substrate comprises one or more discontinuities wherein the one or more discontinuities have a form corresponding to that of the one or more locator pins such that the sample-capture substrate is retainable in position within the enclosed substrate chamber by mutual interaction of the one or more discontinuities and the one or more locator pins.

The one or more locator pins may be situated beneath the element such that the one or more locator pins are inaccessible until the access port is established by the irreversible detachment of at least a part of the element.

The access port may be dimensioned to allow removal of the sample-capture substrate from the enclosed substrate chamber by lifting the sample-capture substrate off the one or more locator pins and sliding the sample-capture substrate laterally relative to the one or more locator pins.

The first part of the housing may comprise a pair of channels and the shutter is slidable within the pair of channels from the first position to the second position.

The retaining mechanism may comprise a protrusion.

The protrusion may be asymmetrical and configured to flex on movement of the second part from the first position into the second position and configured to resist flexing once the second part reaches the second position.

The protrusion may be asymmetrical and may comprise:
a ramp on a first face that permits movement of the second part into the second position; and
a stepped feature on a second face that prevents movement of the second part out of the second position.

The protrusion may be configured to be received within a corresponding detent when the second part of the housing reaches the second position.

The protrusion may be located on the second part of the housing and the detent may be located on the first part of the housing. Alternatively, the protrusion may be located on the first part of the housing and the detent may be located on the second part of the housing.

The element may be located in the first portion of the housing distant the aperture.

The first portion of the housing may be lightproof.

The second portion of the housing may be translucent or transparent.

The sample-capture substrate may comprise an absorbent material.

The sample-capture substrate may be compatible with paper-spray mass spectrometry.

The sample-capture substrate may comprise a non-absorbent material.

The sample capture may enables imaging of the skin-print for record keeping or identification purposes.

It may be that access to the substrate is possible only following immediate visual evidence of tampering.

BRIEF DESCRIPTION OF THE DRAWINGS

Specific embodiments of the invention will now be described, by way of example only, with reference to the accompanying drawings in which.

SPECIFIC DESCRIPTION

Figure 1:
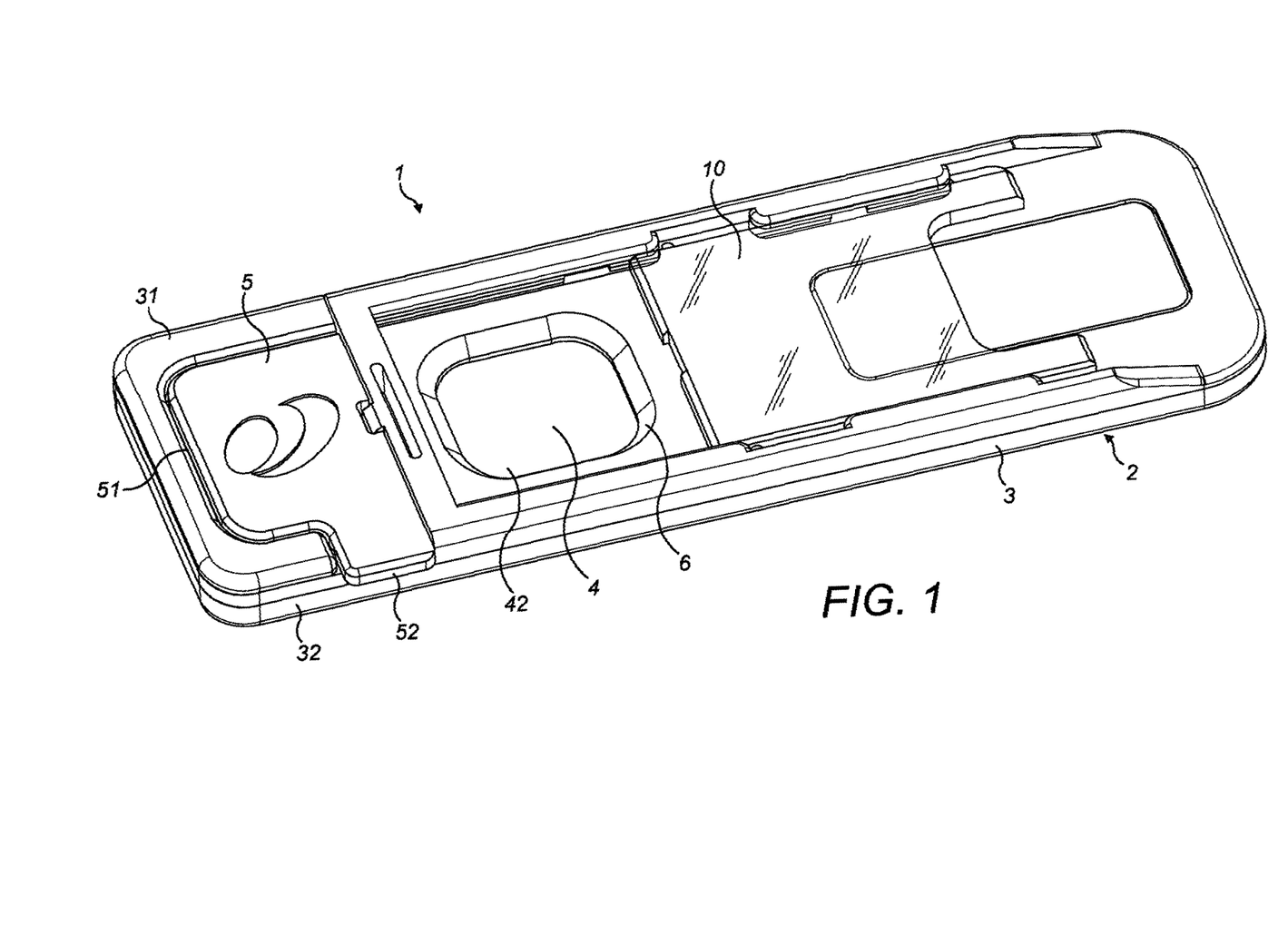
FIG. 1 shows a first embodiment of a sample capture unit of the present disclosure in its primary configuration.
Figure 2:
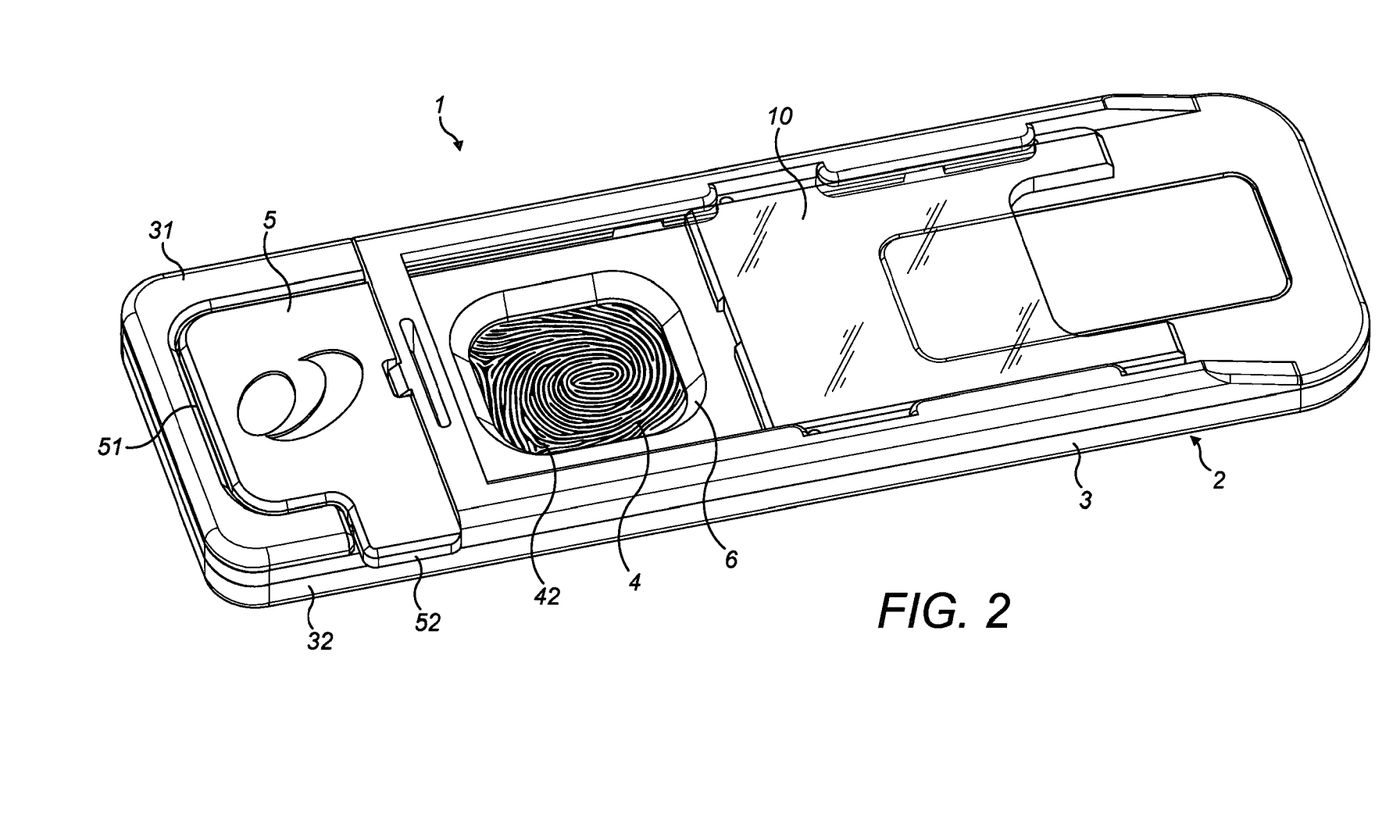
FIG. 2 shows the first embodiment of the present disclosure in its primary configuration with a fingerprint sample deposited.
Figure 3:
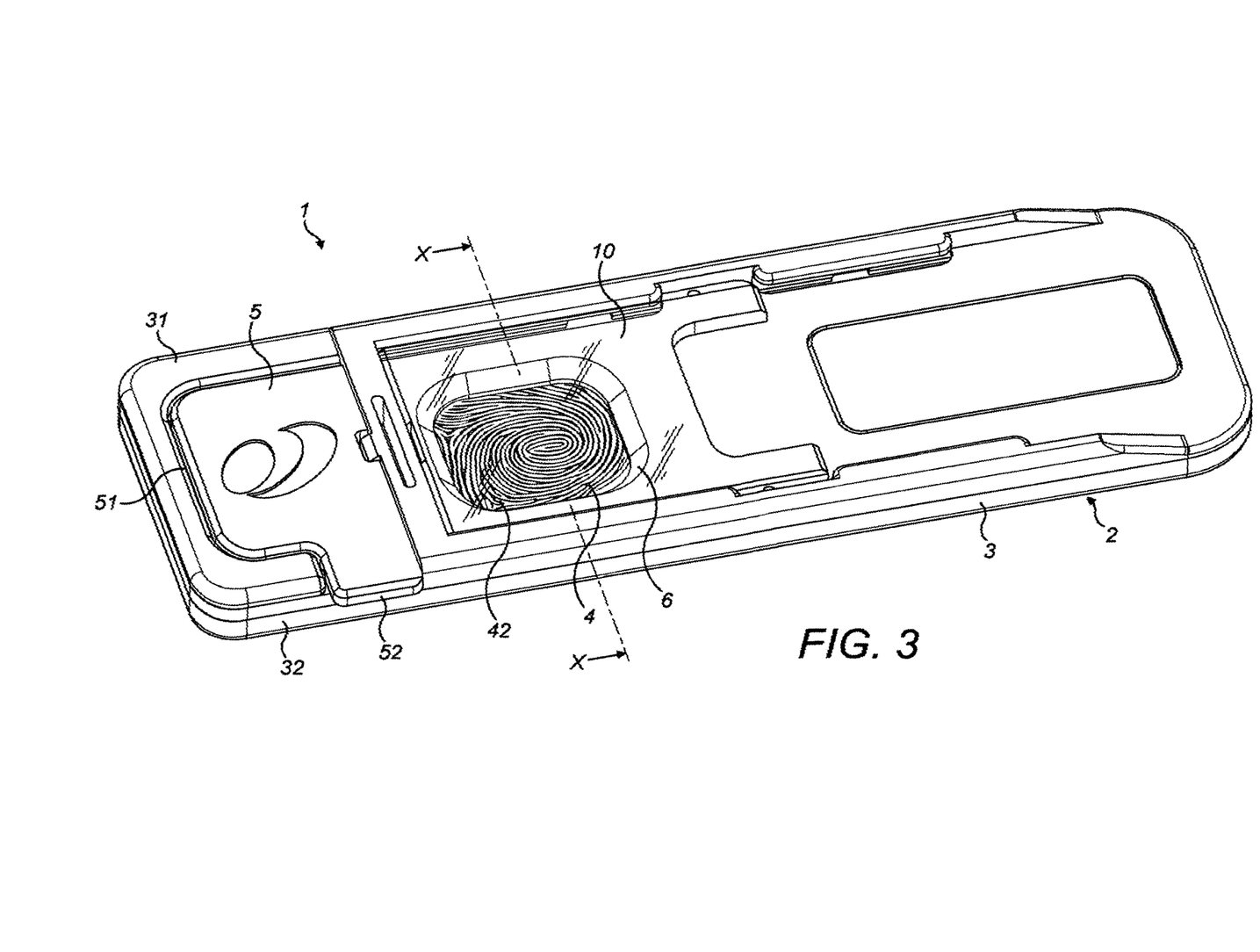
FIG. 3 shows the first embodiment of the present disclosure in its secondary configuration with the fingerprint sample protected from damage and contamination.
Figure 5:
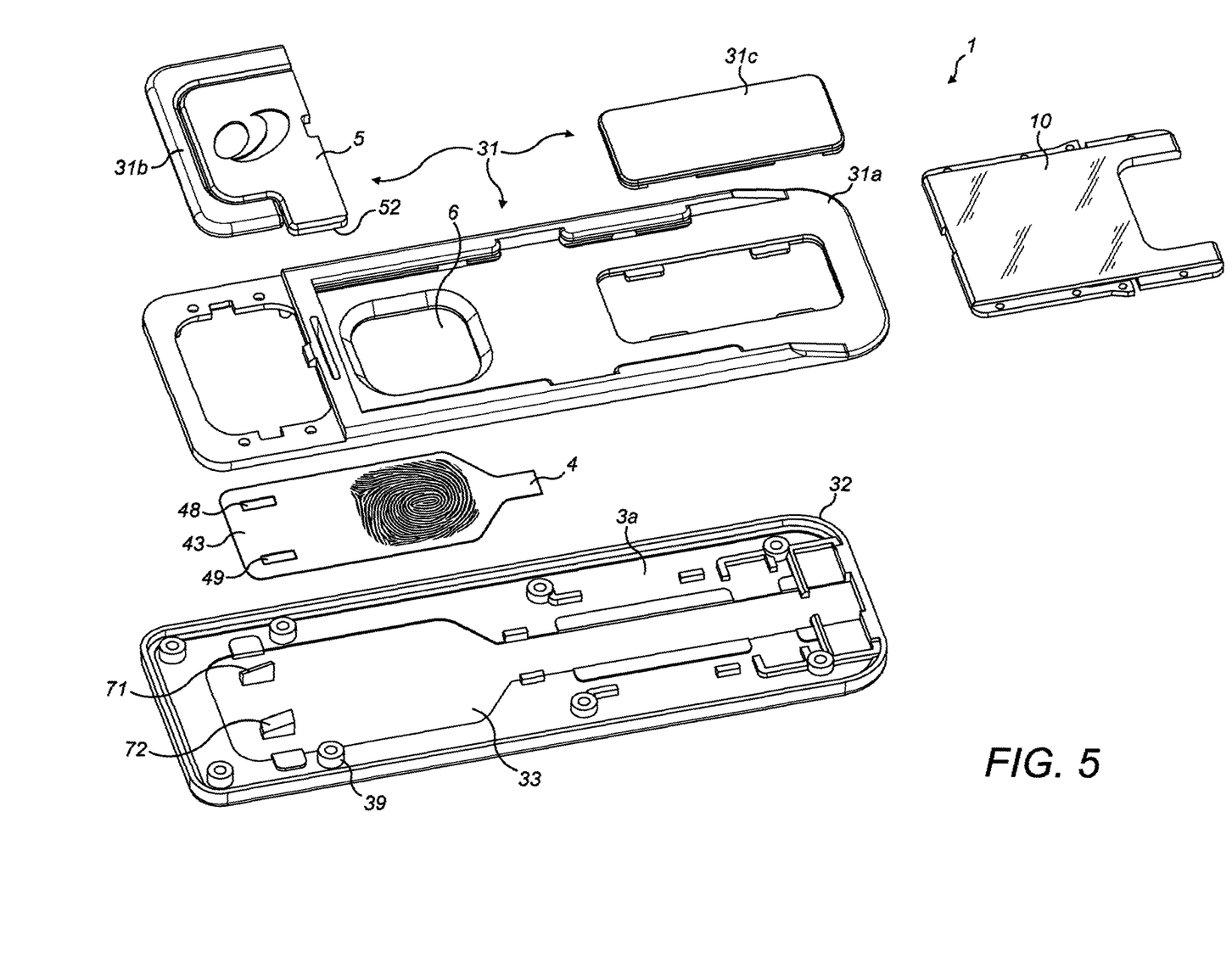
FIG. 5 shows an exploded view of the first embodiment of the present disclosure.
Figure 6:
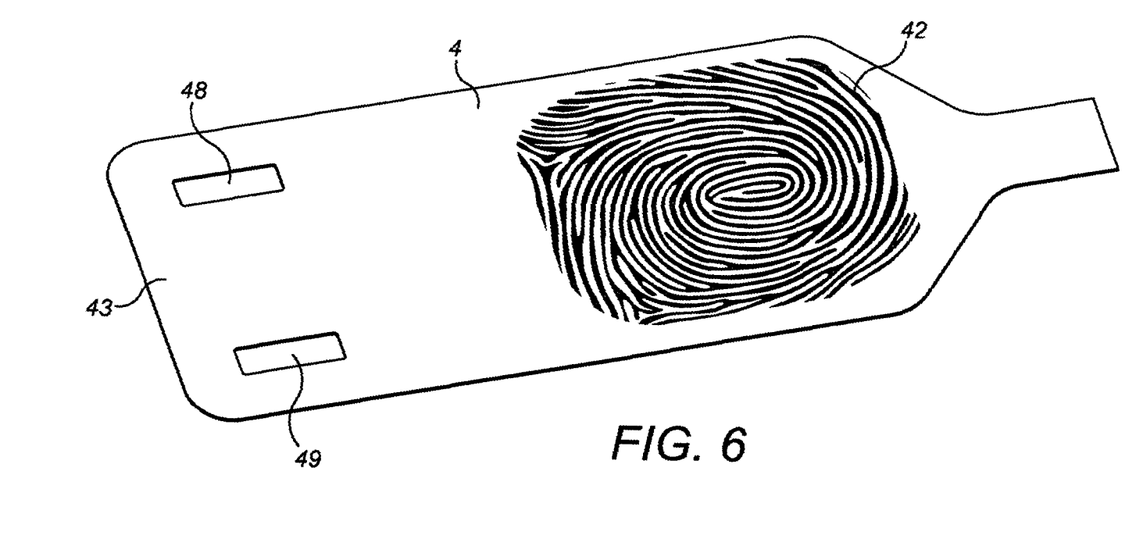
FIG. 6 shows the sample-capture substrate in isolation from the sample capture unit and with a skin-print deposited thereon.
Figure 7:
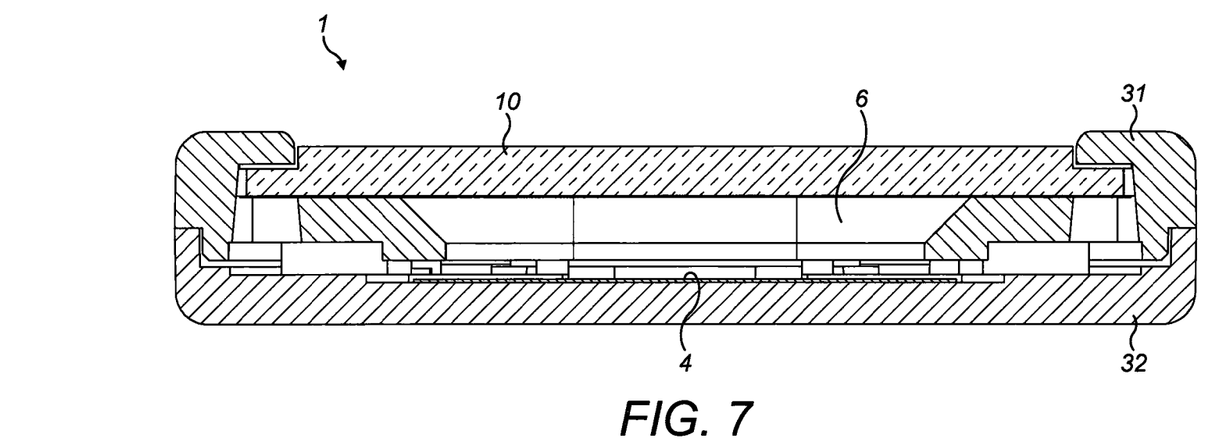
FIG. 7 shows a cross section X-X through the sample capture unit as shown in FIG. 3.

In accordance with a first embodiment, as shown in FIG. 1, there is a sample capture unit 1 for receiving and analysing a sample. The first embodiment is shown in an exploded view in FIG. 5. The sample capture unit 1 may be referred to as a cartridge 1.

The device comprises a housing 2 and a sample receiving material in the form of a substrate 4 that is located within the housing 2. The housing 2 comprises a body 3 having an upper portion 31 and a lower portion 32. The upper portion 31 and the lower portion 32 are manufactured as separate components and then assembled such that the upper and lower portions 31, 32 cannot subsequently be separated. For example, the upper and lower portions 31, 32 may comprise mutually corresponding press-fit or snap-fit features that allow them to be fastened together but which do not permit disassembly. An example of one half of exemplary features 39 is visible in FIG. 5.

On assembly of the upper portion 31 and the lower portion 32 a substrate chamber is formed in a void that is completely enclosed by the housing 2 except for an aperture 6 in the upper portion 31 of the body 3 of the housing 2. The lower portion 32 comprises a recess 33 on an interior surface 3a of the lower portion 32 of the housing. The recess 33 is shaped to receive the substrate 4. The aperture 6 is located relative to the substrate 4 such that the aperture 6 bounds a skin-print receiving region 42 of the substrate 4. The dimensions of the sample window 6 may be configured to allow receipt of at least a part of an area of a skin-print, such as a fingerprint. The dimensions of the sample window 6, and hence the area of the substrate 4 accessible through the sample window 6, may be defined in order to assist in quantitative analysis of constituents in the skin-print. The sample capture unit 1 may enable accommodation of a range of different substrates applicable to a range of different analysis chemistry. The substrate 4 may be selected to enable non-destructive imaging of the biometric of the skin-print.

The housing 2 further comprises a shutter 10 that is slidable relative to the body 3 from a first position to a second position. In the first position, the shutter 10 is distant the aperture 6, thus allowing a fingerprint to be deposited on the substrate 4 via the aperture. In the second position, the shutter 10 covers the aperture 6, meaning that the substrate is entirely enclosed within the housing 2 and is inaccessible from outside the housing 2.

Thus, the housing 2 has a primary configuration in which the shutter 10 is in its first position whereby the aperture 6 is not covered by the shutter 10; and a secondary configuration in which the shutter 10 is in its second position whereby the aperture 6 is covered by the shutter 10.

The body 3 comprises a pair of channels and the shutter 10 is slidable within the pair of channels from the first position to the second position.

The housing comprises a non-return feature that prevents the shutter from being moved out of second position in which the shutter 10 covers the aperture 6. The non-return feature may comprise a retaining mechanism.

The retaining mechanism comprises a protrusion located on the shutter 10 that cooperates with a corresponding feature on the body 3.

The protrusion is asymmetrical and configured to flex on movement of the shutter 10 from the first position into the second position and configured to resist flexing once the shutter reaches the second position.

The protrusion is asymmetrical and comprises a ramp on a first face that permits movement of the shutter into the second position and a stepped feature on a second face that prevents movement of the shutter out of the second position.

The corresponding feature on the body 3 comprises a detent into which the protrusion is received when in the second position.

The substrate 4 is mounted in the housing 2 and anchored relative to the housing 2. In the first embodiment, the anchoring is provided by a pair of pins 71, 72 that protrude from the inner surface 3a of the lower portion 32 of the housing 2. The substrate 4 comprises discontinuities 48, 49 in the form of holes 48, 49. The holes 48, 49 are located and dimensioned relative to the pins 71, 72 such that the pins 71, 72 accommodate the holes 48, 49. In this way, the substrate 4 is prevented from lateral movement or rotational movement in the plane of the substrate. Furthermore, the substrate 4 is prevented from significant movement in a direction parallel to the pins 71, 72 by virtue of the substrate chamber having only a limited height and the pins 71, 72 extending to meet an inner surface of the upper portion 31 of the housing.

The housing 2 is intended to protect the substrate 4 from damage or contamination by preventing access to the substrate 4. The housing 2 may be opaque in order to protect substances that are susceptible to photodegradation which may be present on the substrate 4.

Figure 4:
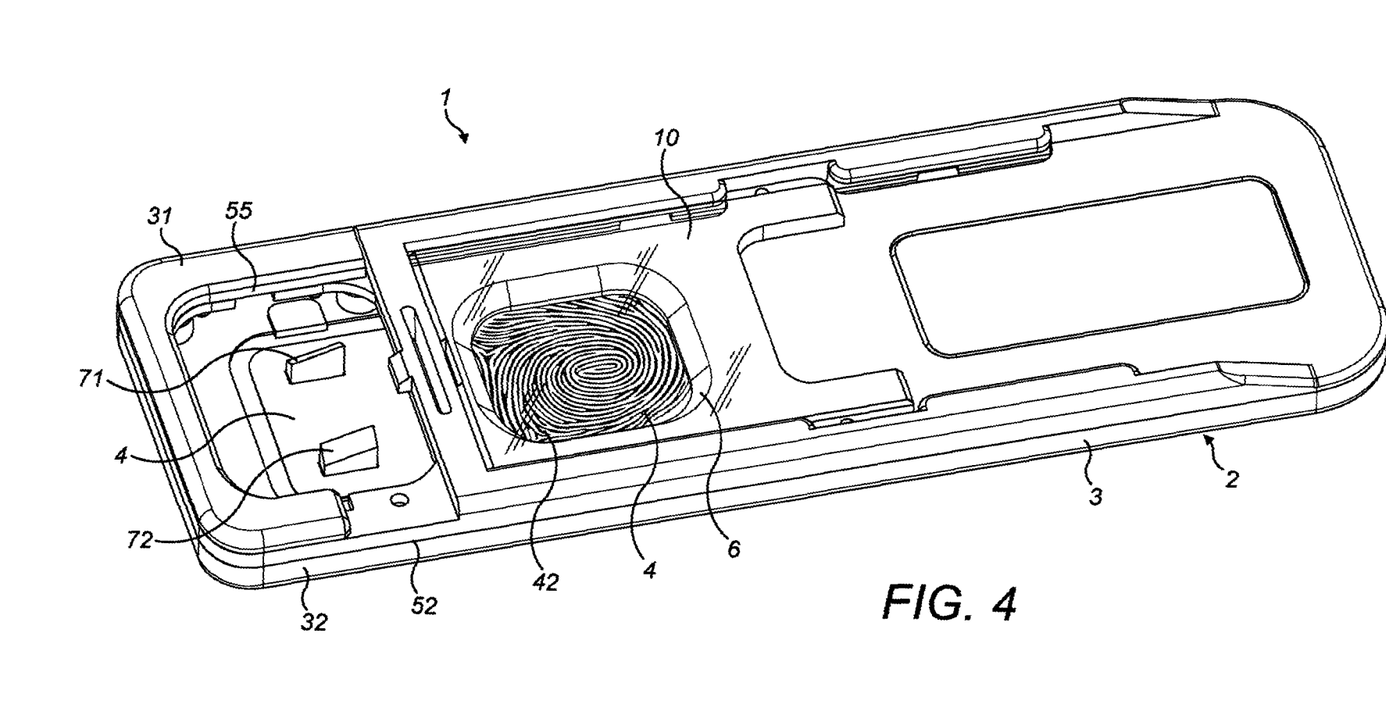
FIG. 4 shows the first embodiment of the present disclosure is tertiary configuration with the snap-off cover removed so as to provide access to the sample-capture substrate for removal from the housing.

The substrate 4, shown in isolation in FIG. 4, comprises the skin-print receiving region 42 and the two holes 48, 49. A skin-print (specifically a fingerprint) is shown deposited on the skin-print receiving region 42 of the substrate 4.

The upper portion 31 of the housing 2 comprises a snap-off element 5 that is located above the pins 71, 72 on the inner surface 3a of the lower portion 32 of the housing 2. The snap-off element 5 is bounded at least substantially by a line of frangibility 51. The line of frangibility 51 may be a region of relative thinner construction of the housing 2.

The snap-off element 5 comprises a tab 52 that extends beyond an exterior shell of the housing 2 in such a way that a user may apply a force to the tab by lifting it such that the housing 2 breaks at the line of frangibility 51 resulting in the snap-off element 5 becoming completely and permanently detached from the housing 2.

FIG. 4 shows the sample capture unit 1 with the element 5 removed so as to provide an access port 55 through which one end of the substrate 4 is revealed beneath. The access port 55 is of a width that is greater than a width of the substrate 4. The substrate 4 may be removed by lifting a first end 43 of the substrate 4 that is adjacent the holes 48, 49 and that is distant the skin-print receiving region 42. In this way, the first end 43 of the substrate 4 may be released from the pins 71, 72 such that lateral movement of the substrate 4 is then possible. This in turn allows the substrate 4 to be removed from the housing 2 by sliding the substrate 4 laterally through the access port 55 provided by the removal of the element 5.

The following section describes the first embodiment of the device, in use.

The sample capture unit 1 may be provided in its primary configuration (as shown in FIG. 1) in which the shutter 10 is in its first position. The sample capture unit 1 may be contained within sealed air-tight packaging such as a laminated bag or foil pouch until immediately prior to use. This provides confidence that the sample capture unit 1 is unused.

Once the sample capture unit 1 is released from the sealed packaging the skin-print receiving region 42 of the substrate 4 is accessible and a user is invited to deposit a skin-print, most likely a fingerprint, on the skin-print receiving region 42 of the substrate 4.

Once a skin-print has been deposited on the skin-print receiving region 42 of the substrate 4, the shutter 10 is moved from the first position to the second position. Accordingly, the shutter 10 covers the sample window 6 thus preventing access to the substrate 4. This forms the secondary configuration of the sample capture unit 1.

The sample capture unit 1 may then be transported to another location for analysis.

When ready for analysis, the snap-off element 5 may be detached from the housing 2 by a user pulling on the protruding tab 52 to as to apply a force to the line of frangibility 51 until the snap-off element 5 is detached from the housing. Removal of the snap-off element 5 brings the sample capture unit 1 into its tertiary configuration in which the access port 55 provides access to the substrate 4. The tertiary configuration allows the substrate 4 to be released from the pins 71, 72 and removed from the sample capture unit 1 via the access port 55. The housing 2 may then be disposed of appropriately, for example by recycling. Relative to samples involving bio-hazardous material (e.g. blood or urine), when used to receive a skin-print on the substrate, the housing 2 is appropriate for non-hazardous disposal.

The housing 2 may be formed in three, four or five parts from high density polystyrene (HDPS). In a three-part configuration, the three parts are the upper portion 31 of the housing, the lower portion 32 of the housing and the shutter 10. The housing 2 of the first embodiment is a five part embodiment, as shown most clearly in FIG. 5. In the five part configuration, the lower portion 32 and the shutter 10 are as in the three-part configuration. The upper portion 31 comprises three parts, namely a main part 31a, an element assembly 32b which includes the element 5 and its surroundings, and a blanking part 31c which blocks a hole in the main part 31a. In this embodiment, the three components of the upper portion 31 may snap-fit together in an irreversible manner. The reason for an upper portion 31 being formed of three components may be allow the reuse of moulds provided for other sample capture units, for example a sample capture unit configured for in situ lateral flow analysis.

One possible application of the sample capture unit of the present disclosure is to enable analysis by paper spray spectrometry of a sample deposited on the substrate. The substrate may be chromatography paper such as Whatman grade 1 chromatography paper having a thickness of 0.18 mm. Alternatively, the substrate may comprise Whatman Grade 31ET chromatography paper (thickness 0.508 mm). Functionalised cellulose paper (ion exchange papers and Whatman DMPK paper) might also be used. In some circumstances it may be beneficial to treat the substrate prior to use. Other substrates fall within the scope of the disclosure.

In other applications, the substrate may comprise a rigid material such as glass or plastic. More specifically, the substrate may be of polyethylene terephthalate (PET). The PET may be of a thickness of approximately 100 µm. The PET may incorporate a non-hydroscopic moisture barrier structure. This may be particularly useful in enabling sweat compounds present in a skin-print deposited thereon to be isolated and analysed without contaminants. Use of PET that is of a sufficiently small thickness to enable it to be rolled up may facilitate the ability to process the sample in a test tube.

In a specific implementation, the PET may be placed in a solubilisation extraction solution and a sample of the solution may be extracted for analysis using mass spectrometry.

Alternative Embodiments

In an alternative embodiment, shutter 10 is movable with respect to the body 3 from a first position in which the shutter is closed, to a second position in which the shutter is open (corresponding to the first position of the first embodiment) and into a third position in which the shutter is closed again and in which the shutter is locked in position (corresponding to the second position of the first embodiment). The locking in the third position may be provided by an anti-tamper latch. This may mean that it is not necessary to provide the sample capture unit 1 in a sealed bag since the substrate 4 is protected by the shutter prior to use.

It is not essential that the element 5 having a perimeter defined by a line of frangibility 51 is completely detached from the housing 2. For example, it may be that the element 5 remains connected to the housing 2 at one point or along one line. For example, the element 5 may remain hingedly attached to the housing 2. In this way, as in the first embodiment, it is immediately self-evident that the line of frangibility 51 has been exploited such that there is no longer confidence that the substrate 4 has been inaccessible, but the element 5 remains in some way connected to the housing 2 in a limited fashion.

While in the first embodiment the line of frangibility 51 comprises a region of the housing 2 of reduced thickness relative to the majority of the housing 2, it is possible that the line of frangibility 51 may be provided by other techniques. For example, the line of frangibility 51 may be a region of the housing 2 that undergoes treatment, for example laser treatment, that results in the treated region 51 becoming preferentially brittle. This may be particularly relevant if the perimeter of the element 5 is spatially more complex than in the first embodiment.

In alternative embodiments, it may be that the snap-off element 5 may be in a different location from that disclosed in respect of the first embodiment. For example, the snap-off element 5 may be located on the lower portion 32 of the body 3 of the housing 2. In a further alternative, it may be that the snap-off element 5 is located on the shutter 10.

The invention claimed is:

1. A sample capture unit comprising a housing defining an enclosed substrate chamber containing a substantially planar sample-capture substrate extending in a plane for receiving a skin-print thereon, the housing comprising:
   a first part having an aperture providing access to the substrate chamber for depositing a skin-print on the sample-capture substrate;
   a second part movable relative to the first part:
      from a first position in which the aperture is uncovered so as to allow receipt of a sample on the sample-capture substrate; and
      into a second position in which the aperture is covered, thereby preventing access to the substrate chamber; and
   a retaining mechanism configured to retain the second part in the second position;
   wherein the housing further comprises an element having a perimeter defined by a line of frangibility which enables irreversible detachment of at least a part of the element so as to create an access port dimensioned to allow removal of the sample-capture substrate.

2. The sample capture unit of claim 1 wherein the element is a snap-off cover, the snap-off cover being partially or fully detachable from the housing by irreversible breaking at the line of frangibility.

3. The sample capture unit of claim 1 wherein the housing comprises an exterior shell and the element comprises a tab that protrudes beyond the exterior shell by which a user may apply a force to the element to effect detachment of at least a part of the element by breaking at the line of frangibility.

4. The sample capture unit of claim 1 wherein the second part of the housing comprises a shutter slidable with respect to the first part of the housing.

5. The sample capture unit of claim 4 wherein the first part of the housing comprises a pair of channels and the shutter is slidable within the pair of channels from the first position to the second position.

6. The sample capture unit of claim 1 wherein the substantially planar sample-capture substrate has a length and a width in the plane, wherein the width is smaller than the length, and wherein the access port has a dimension that is larger than the width of the sample-capture substrate.

7. The sample capture unit of claim 1 wherein the aperture is laterally offset from the element in the plane.

8. The sample capture unit of claim 1 wherein the enclosed substrate chamber comprises one or more locator pins and the sample-capture substrate comprises one or more discontinuities wherein the one or more discontinuities have a form corresponding to that of the one or more locator pins such that the sample-capture substrate is retainable in position within the enclosed substrate chamber by mutual interaction of the one or more discontinuities and the one or more locator pins.

9. The sample capture unit of claim 8 wherein the one or more locator pins are situated beneath the element such that the one or more locator pins are inaccessible until the access port is established by the irreversible detachment of at least a part of the element.

10. The sample capture unit of claim 9 wherein the access port is dimensioned to allow removal of the sample-capture substrate from the enclosed substrate chamber by lifting the sample-capture substrate off the one or more locator pins and sliding the sample-capture substrate laterally relative to the one or more locator pins.

11. The sample capture unit of claim 1 wherein the retaining mechanism comprises a protrusion, and optionally wherein the protrusion is asymmetrical and configured to flex on movement of the second part from the first position into the second position and configured to resist flexing once the second part reaches the second position.

12. The sample capture unit of claim 11 wherein the protrusion is asymmetrical and comprises:

a ramp on a first face that permits movement of the second part into the second position; and a stepped feature on a second face that prevents movement of the second part out of the second position.

13. The sample capture unit of any of claim 11 wherein the protrusion is configured to be received within a corresponding detent when the second part of the housing reaches the second position, and optionally wherein the protrusion is located on the second part of the housing and the detent is located on the first part of the housing;

or wherein the protrusion is located on the first part of the housing and the detent is located on the second part of the housing.

14. The sample capture unit of claim 1 wherein the element is located in the first portion of the housing distant the aperture.

15. The sample capture unit of claim 1 wherein the first portion of the housing is lightproof.

16. The sample capture unit of claim 1 wherein the second portion of the housing is translucent or transparent.

17. The sample capture unit of claim 16 wherein the sample-capture substrate comprises an absorbent material, and wherein optionally the sample-capture substrate is compatible with paper-spray mass spectrometry.

18. The sample capture unit of claim 16 wherein the sample-capture substrate comprises a non-absorbent material.

19. The sample capture unit of claim 1 which enables imaging of the skin-print for record keeping or identification purposes.

20. The sample capture unit of claim 1 wherein access to the substrate is only possible following immediate visual evidence of tampering.

* * * * *